(12) United States Patent
Wuttke et al.

(10) Patent No.: US 7,413,754 B2
(45) Date of Patent: Aug. 19, 2008

(54) **USE OF EXTRACTS OF THE GENUS *CIMICIFUGA* AS ORGANOSELECTIVE MEDICINES FOR TREATING DISEASES OF THE GENITOURINARY SYSTEM CAUSED BY SEX HORMONES**

(75) Inventors: Wolfgang Wuttke, Bovenden (DE); Hubertus Jarry, Neu-Eichenberg (DE); Volker Christoffel, Buchberg (DE); Barbara Spengler, Neumarkt (DE)

(73) Assignee: Bionorica AG, Neumarkt (DE)

( * ) Notice: Subject to any disclaimer, the term of this patent is extended or adjusted under 35 U.S.C. 154(b) by 288 days.

(21) Appl. No.: 10/490,190

(22) PCT Filed: Sep. 16, 2002

(86) PCT No.: PCT/EP02/10383
§ 371 (c)(1),
(2), (4) Date: Sep. 13, 2004

(87) PCT Pub. No.: WO03/024465
PCT Pub. Date: Mar. 27, 2003

(65) Prior Publication Data
US 2005/0019437 A1 Jan. 27, 2005

(30) Foreign Application Priority Data
Sep. 19, 2001 (DE) .............................. 101 46 159

(51) Int. Cl.
*A61K 36/00* (2006.01)
(52) U.S. Cl. ................................................. 424/725
(58) Field of Classification Search .................. None
See application file for complete search history.

(56) References Cited

U.S. PATENT DOCUMENTS

| | | | |
|---|---|---|---|
| 5,382,430 A | 1/1995 | Soma et al. | |
| 5,411,733 A | 5/1995 | Hozumi et al. | |
| 5,569,459 A | 10/1996 | Shlyankevich | |
| 5,716,646 A | 2/1998 | Smith et al. | |
| 5,795,574 A | 8/1998 | Breton et al. | |
| 5,916,565 A * | 6/1999 | Rose et al. | 424/756 |
| 5,952,374 A | 9/1999 | Clarkson, Jr. et al. | |
| 6,008,208 A | 12/1999 | Petrie et al. | |
| 6,242,012 B1 | 6/2001 | Newmark et al. | |
| 6,267,994 B1 | 7/2001 | Nesselhut | |
| 6,326,366 B1 | 12/2001 | Potter et al. | |
| 6,471,997 B1 | 10/2002 | Breton et al. | |
| 2001/0025059 A1* | 9/2001 | Kastke | 516/70 |
| 2002/0010141 A1 | 1/2002 | Ingram | |
| 2002/0172732 A1 | 11/2002 | Ter Laak et al. | |

FOREIGN PATENT DOCUMENTS

| | | |
|---|---|---|
| CN | 1090498 | 8/1994 |
| CN | 1158261 | 9/1997 |
| CN | 1159340 | 9/1997 |
| CN | 11158261 A | 9/1997 |
| DE | 361762 C2 | 6/1992 |
| EP | 0847755 | 11/1997 |
| HU | 204 197 | 12/1991 |
| JP | 63030417 A | 2/1988 |
| JP | 63030417 | 9/1988 |
| JP | 07138179 | 5/1995 |
| JP | 07138181 | 5/1995 |
| JP | 07138181 A | 5/1995 |
| JP | 09030977 A | 2/1997 |
| JP | 09-124499 | 5/1997 |
| JP | 09-0301884 | 11/1997 |
| JP | 10-007580 | 1/1998 |
| JP | 10-084923 | 4/1998 |
| WO | WO 97/09056 | 3/1997 |
| WO | 9715398 | 5/1997 |
| WO | WO 99/47419 | 9/1999 |
| WO | WO 01/74345 A2 | 10/2001 |
| WO | WO 02/36140 | 5/2002 |
| WO | WO 02/007321 A1 | 9/2002 |

OTHER PUBLICATIONS

Gura; Science (1997), vol. 278, pp. 1041-1042.*
Milewicz, A., et al, "Vitex agnus castus-Extrakt zur Behandlung von Regeltempoanomalien infolge latenter Hyperprolaktinamie," Arzneimittel Forsch 43: 752-756 (1993 in German).
Hoberg, E., et al., "Diterpenoids from the Fruits of Vitex agnus-castus," Phytochemistry 52: 1555-1558 (1999).
Gorkow, "Klinischer Denntnisstand von Agni-casti fructus," Z. Phytotherapie 20: 159-168 (in German), 1999.
Einer-Jensen, N., et al., "*Cimicifuga* and Melbrosia Lack Oestrogenic Effects in Mice and Rats," Maturitas 25: 149-153 (1996).

(Continued)

*Primary Examiner*—Susan C Hoffman
(74) *Attorney, Agent, or Firm*—Catalyst Law Group, APC; Michael B. Farber

(57) ABSTRACT

The present invention relates to extracts from *Cimicifuga* species and particularly from *Cimicifuga racemosa*, which are suited for producing a ready-formulated drug for the selective treatment and/or prophylaxis of sexual hormone-related disorders of the uro-genital tract. The extracts in accordance with the invention are moreover suited for the treatment and/or prophylaxis of post-menopausal urinary bladder infections. They are furthermore indicated for the treatment of benign and malignant prostate hyperplasies.

6 Claims, 1 Drawing Sheet

OTHER PUBLICATIONS

Rote Liste 1986 (Editio Cantor, Aulendorf, Wurttemburg).

Esaki, S., "Pharmacological Studies of Tectoridin and Tectorigenin," Nippon Yakurigaku Zasshi 64: 186-198 (1968).

Petersen, F.J., Materia Medica and Clinical Therapeutics, "*Cimicifuga racemosa*," 1905.

Li, J.X., et al, "Effects of Cimicifugae Rhizoma on Serum Calcium and Phosphate Levels in Low Calcium Dietary Rat . . . ," Phytomedicine 3:379-385 (1996/97).

Duker, E.-M., et al., "Die Wirking von Extrakten aus *Cimicifuga racemosa* auf die Gonadotropinfreizetzung in Menopausalen Frauen und . . . ", Planta Med. 57:420-424 (1991).

Sorrentino, L. and Genazzanai. E., "Vascular Action of Acteina: Active Constituent of *Actaea raemosa* L.," Nature 12:544-545 (1962).

Kumar, T., and Shawl, A.S., "Isoflavonoids from *Iris crocea*," Phytochemistry 31: 1399-1401 (1992).

Lin, M. and Zhou, L.X., "Studies on Chemical Constituents of *Belamcanda chinensis* (L.) DC (II)," Chin. Chem. Lett. 8:133-134 (1997).

Wooten, G., "The Herbal Database," 1984, www.okanoganl.com/natural/chem/hrbdata.htm.

List, P.H. and Horhammer, L., eds., An Hagers Handbuch der Pharmazeutischen Praxis (4th ed., Springer-Verlag, Berlin, 1972), vol. 3 pp. 375-376 (in German).

Jarry, H., et al., "Treatment of Menopausal Symptoms with Extracts of *Cimicifuga racemosa*: In viv . . . ," Phytopharmaka Forsch. Klin, Anwend 99-122 (1995).

Homoopathisches Arzneibuch 2000 (Deutscher Apotheker Verlag Stuttgart), entitled "*Iris versicolor*,".

F. Borrelli & E. Ernst, "*Cimicifuga racemosa*: A systematic review of its climical efficacy," Eur.J.Clin.Pharmacol. 58: 235-241.

J. Liu, et al., "Evaluation of Estrogenic Activity of Plant Estracts for the Potential Treatment of Menopausal Sumptoms," J.Agric. FoodChem. 49: 2472(2001).

C. Willis, "Herb to Know—Black Cohosh—*Cimicifuga racemosa*," at http://www.wisetouch.com/blackcohosh.html, published May 22, 2002.

Montemuro, Dr. Suzanne, "Alternatives to H.R.T. and the Menopausal Woman," The Soc. of Obstetricians and Gynaecologists of Canada, 1996, Publ. May 22, 2002.

Kawase, A., et al., "Flavonoid of Iridacea. II. Chemical Structure of ao New Isoflavone Glucoside, Homotectoridin, Isolated Together with Tectoridin from the Rhizomes of *Iris germanica*," Agric. & Biol. Chem. (1973), pp. 145-150, V. 37 (abstract).

Pailer, M. & Franke, F., "Constitutes of *Iris germanics*," Monatsh. Chem., (1973), pp. 1394-1408, V. 104 (abstract).

Li, Y., et al., "Flavonoids of *Iris dichotoma* Pall," Yaoxue Xuebao, (1986), pp. 836-841, V. 21 (abstract).

Lu, Y., et al., "Quantitative Analysis for the Three Main Isoflavonoids in the Chinese Drug, Shegan, by TLC/HPLC-Densitometry," Yaowu Fenxi Zazhi, (1987), pp. 275-279 V. 7, abstract.

Huang, M., "Studies on the TLC and Assay of *Belamcanda chinensis* (L.) DC, *Iris tectorum* Maxim and *Iris dichotoma* Pall," Yaowu Fenxi Zazhi, (1997), pp. 112-115, V. 17 (abstrac.

Eskai, S., et al., "Physiological Studies on Tectoridin and Tectorigenin," Nippon Yakurigaku Zasshi, (1968), pp. 186-198, V. 64 (in Japanese), entire article.

Web page: "Garden Web's Hortiplex Plant Database", at: http://hortiplex2.gardenweb.com/plants/p1/gw1020997/html—accessed Dec. 19, 2004.

Web page: "Iris pallida illyrica", at: http://www.zaplana.net/flowers/asp/display_flower [Zaplana.net]—accessed Dec. 16, 2004.

Diel, P. et al., "Ability of xeno- and pythoestrogens to odulate expression of estrogen-sensitive genes in rat uterus . . . ," J. Steroid Biochem. Mol.Biol. 73:1-10 (2000).

Whitten, P. & H.B. Patisaul, "Cross-species and interassy comparisons of phytoestrogen action," Environ.Health Perspect. 109s1: 5-20 (2001).

Blaschek, W. et al., eds., "Drogen A-K", Folgeband 2 (Springer-Verlag, Berlin, 1998), pp. 374-378 (in German).

Pschyrembel, "Wörterbuch Naturheilkunde und alternative Heilverfahren" (Walter de Gruyter, Berlin, 1996), p. 52 (in German).

Ezaki, S., "Pharmacological Effects of Tectoridin and Tectorigenin," J. Japan Pharmacol. Assoc. (1968), 64:186-198.

S. Ezaki, "Pharmacological Studies of Tectoridin and Tectorigenin," Nippon Yakurigaku Zasshi 64: 186-198 (1968) (original publication in Japanese), Chemical Abstracts, v. 69, p. 9822, Abstract No. 104972j.

J.X. Li et al., "Anti-Osteoporotic Activity of Traditional Medicines—Active Constituents of Cimicifugae Rhizome," J. Tradit. Med. 12:816-817 (1995).

H. Jarry & G. Harnischfeger, "Studies on the Endocrine Effects of the Contents of *Cimicifuga racemosa* 1. Influence on the Serum Concentration of Pituitary Hormones in Ovariectomized Rats," Planta Medica 1:46-49 (1985).

H. Jarry et al., "Studies on the Endocrine Effects of the Contents of *Cimicifuga racemosa* 2: In Vitro Binding of Compounds to Estrogen Receptor," Planta Medica 4:316-319 (1985).

E.-M. Duker et al., "Effects of Extracts of *Cimicifuga racemosa* on Gonadotropin Release in Menopausal Women and Ovariectomized Rats," Planta Med. 57:420-424 (1991).

Revilla et al., "Comparison of Several Procedures Used for the Extraction of Anthocynains from Red Grapes," J. Agric. Chem. 46:4592-4597 (1998).

Phillipson, "New Drugs from Nature—It Could Be Yew," Phytotherapy Research 13:2-8 (1999).

Pereira et al., "Plant and Plant-Derived Compounds Employed in Prevention of Osteoporosis," Acta. Farm. Bonaerense 21(3):223-34 (2002).

Ososki et al., "Phytoestrogens: A Review of the Present State of Research," Phyto. Res. 174:845-869 (2003).

\* cited by examiner

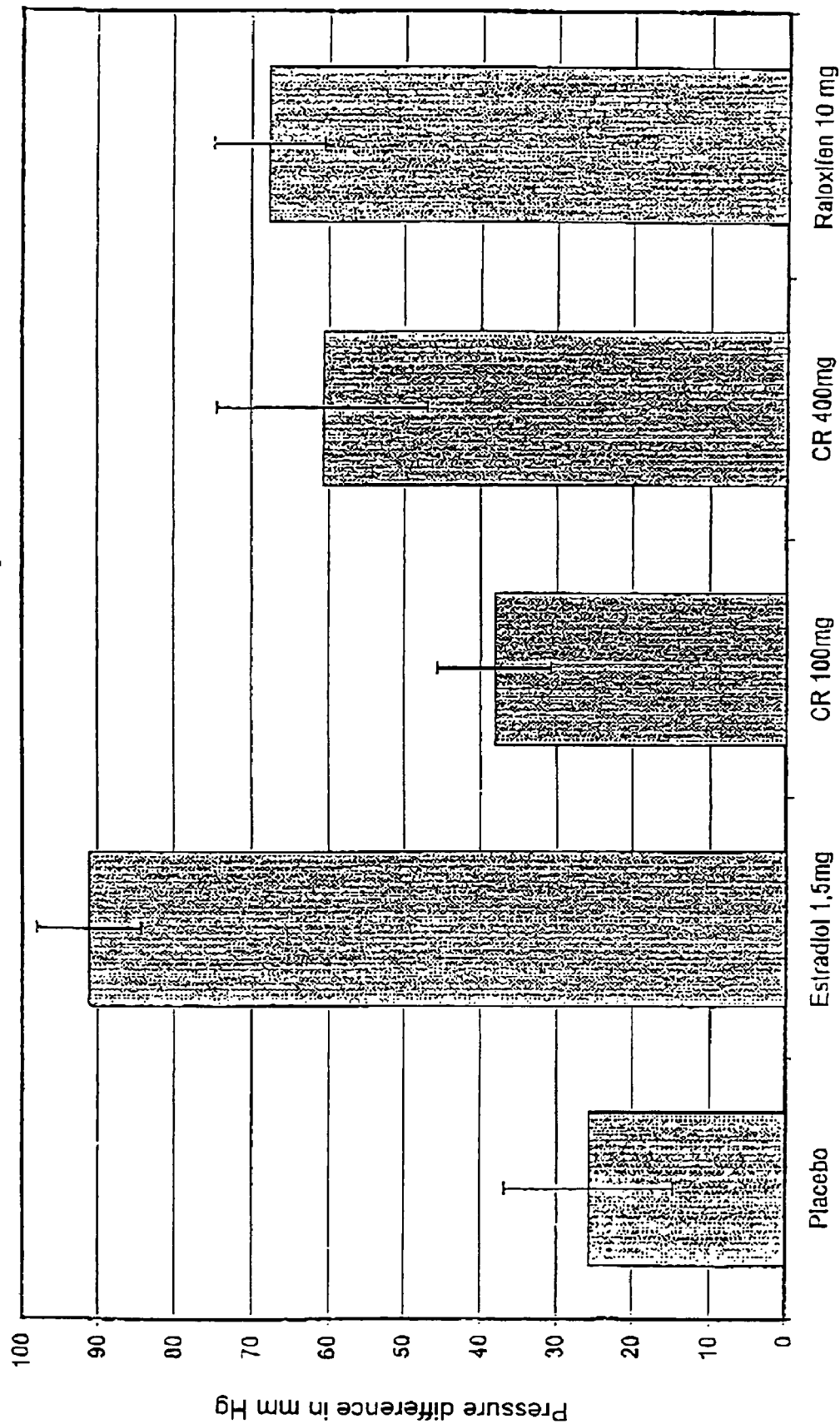

ized in the rat by testosterone. In analogy with the findings in the case of castrated rats not treated with androgen (see above), the IGF1 expression regulated up by testosterone (see above) could also be regulated down by the *Cimicifuga*

USE OF EXTRACTS OF THE GENUS *CIMICIFUGA* AS ORGANOSELECTIVE MEDICINES FOR TREATING DISEASES OF THE GENITOURINARY SYSTEM CAUSED BY SEX HORMONES

The present invention relates to a use of extracts from *Cimicifuga* species.

It is known from WO99/47149 (=EP1064009A1) to the applicant of the present application that extracts from *Cimicifuga racemosa* have an estrogenic effect not on the uterus, however in the hypothalamo-hypophysary axis, in the cardiovascular system, and in the bone. Insofar extracts from *Cimicifuga racemosa* have been utilized in order to produce an estrogen-type, organoselective medicament having no uterotrophic effect.

17β-estradiol, which is formed in women's ovaries (any mention of estradiol hereinbelow refers to physiological 17β-estradiol) [hereinafter also referred to as $E_2$], has a generally proliferation-enhancing effect in the organism. In addition to controlling the female cycle, it i. a. also has a homeostatic effect on the functions of urethra, bladder, and vagina. In men, locally formed estradiol as well as the male sexual hormone testosterone also have a proliferation-enhancing effect in the bladder and in the prostate.

During menopause, lowering of the estradiol level takes place due to cessation of the ovarial function. This results in weakening of proliferative processes in many organs, with subsequently occurring degeneration and reduced functional capacity.

With lack of estrogen, cystitis frequently develops in the post-menopausal woman as a consequence of reduced mucous membrane in the urethra and thus facilitated ascension of germs.

Urinary incontinence frequently occurring post-menopausally is equally caused by lack of estrogen. These disorders may be prevented or alleviated, respectively, by timely administration of estradiol.

Hormonal regulation of the function of the bladder in men presumably is similar to that in women; in any case the hitherto known regulative principles in the urinary bladder of male and female rats are very similar.

The administration of estrogens having a nonselective proliferative action is particularly adverse for uterus and breast tissue, for uncontrolled growth may occur here owing to the insufficiency or lack of gestagen counter-regulation.

Up to the present, there is no medicament available from plant drugs that might be used for an organoselective prophylaxis or therapy of changes in the uro-genital tract in the event of estrogen deficiency.

Starting out from this prior art, it accordingly is an object of the present invention to furnish plant medicaments having a sexual hormone-type action while having an organoselective action with no effect or only little effect on the uterus.

This object is achieved through the use of extracts from *Cimicifuga* species, particularly *Cimicifuga racemosa*.

In particular, the present invention relates to
use of extracts from *Cimicifuga* species, particularly *Cimicifuga racemosa*, for producing an estrogen-type organoselective medicament having no uterotrophic effect or one that is at least negligible, wherein
the medicament is used for alleviating sexual hormone-related disorders of the uro-genital tract.
Use is preferred in the following, post-menopausally occurring disorders: cystitis and dry vagina.
Moreover the present invention relates to a use of extracts from *Cimicifuga* species, particularly *Cimicifuga racemosa*, for producing an estrogen-type organoselective medicament having no uterotrophic effect or one that is at least negligible, wherein
the medicament is utilized for alleviating benign and malignant prostate hyperplasy.

It was surprisingly found that *Cimicifuga racemosa* extract, for example from the rhizoma of *Cimicifuga racemosa*, also has effects similar to those of estradiol in the urinary bladder and in the urethra of ovarectomized rats. In the bladder both the estrogen receptor ER-alpha and ER-beta are expressed. It was found that estradiol and *Cimicifuga* analogously regulate down the gene expression of the estrogen receptor-alpha in the urinary bladder. Thus it appears that besides innervation, the bladder tonus may also be influenced through steroid hormones.

FIG. 1 shows a diagram which represents the differential bladder tonus of ovarectomized rats (group sizes: 12 animals). Following a three-month treatment of ovarectomized rats with *Cimicifuga racemosa* extract, the maximum pressure in the urinary bladder [in mm Hg] and the minimum pressure [in mm Hg] following relaxation of the bladder were determined by instillation of 1 ml of physiological saline solution.

The diagram in accordance with FIG. 1 shows on the ordinate the differential pressure [in mm Hg] between maximum and minimum pressure, which is an indication for the elasticity of the urinary bladder.

In comparison with placebo controls following a treatment with *Cimicifuga* extract, a significant dosage-dependent increase of bladder elasticity, measured through the pressure difference between relaxed and definedly filled bladder, is found.

In the test system, estradiol is found to be the most effective substance.

The highest *Cimicifuga* dose (400 mg/kg/d) triggers an effect comparable to that of the synthetic SERM (Selective Estrogen Receptor Modulator), Raloxifen.

Thus an additional effect of the extract on the urinary bladder, namely, an improvement of bladder incontinence, is equally proven.

Benign prostate hyperplasy and prostate carcinoma in men may also be influenced favorably by inhibition of the local estrogen production, but also by inhibiting synthesis of the male sexual hormones.

The like active mechanisms may also be demonstrated on the male castrated rat for the *Cimicifuga racemosa* extract. In the course of trials by the inventors of the present application, it was found that estradiol and the *Cimicifuga* extract significantly inhibit gene expression of the estrogen receptor of the alpha-subtype in the prostate without having an effect on the gene expression of the estrogen receptor-beta.

Both in in-vivo experiments in the rat prostate in the whole-body model and in human prostate carcinoma cells it was surprisingly found that *Cimicifuga racemosa* extracts have an anti-androgenic action favorably influencing prostate carcinoma and significantly inhibiting growth of the tumor cells in vitro.

In the prostate of castrated male rats, gene expression of the proliferation-enhancing growth factor IGF1 is moreover regulated up by testosterone, however regulated down by *Cimicifuga*, as is desired for reducing the hyperplasy. The prostate regression induced by castration could be antagonized in the rat by testosterone. In analogy with the findings in the case of castrated rats not treated with androgen (see above), the IGF1 expression regulated up by testosterone (see above) could also be regulated down by the *Cimicifuga* extract. These findings clearly demonstrate that the testosterone-induced prostate growth may be inhibited by extracts from *Cimicifuga* species.

In experiments on the human prostate-Ca line LNCAP, 5 alpha-dihydrotestosterone-induced proliferation and the production of its prostate-specific antigen (PSA) may significantly be inhibited by *Cimicifuga* species, particularly *Cimicifuga racemosa*.

Inasmuch as IGF1 always participates in the proliferation not only of benign but also malignant tumors, the inhibitory effect of extracts from *Cimicifuga* species on IGF1-gene expression in conjunction with this finding is evidence for an inhibitory effect on the prostate carcinoma.

As regards manufacture of the extract in accordance with the invention, WO99/47 149 is herewith fully included herein by reference, the essential features of which are, however, presently summarized as follows:

It was found through in-vitro and in-vivo experimentation that extracts produced both from *Cimicifuga* species, particularly *Cimicifuga racemosa*, with organic solvents or mixtures of organic solvents with water or with supercritical $CO_2$ have an organoselective effect on the uro-genital system, with an effect on the uterus being absent.

Thus the extracts used in accordance with the invention are suited for producing a ready-formulated medicament for the selective treatment and/or prophylaxis of sexual hormone-related disorders of the uro-genital tract.

Furthermore they are suitable for producing a ready-formulated medicament for the selective treatment and/or prophylaxis of post-menopausal urinary bladder infections.

They are moreover suited for producing a ready-formulated medicament for the treatment of benign and malignant prostate hyperplasies.

It was moreover found that enriched and/or pure ingredients or groups of ingredients from *Cimicifuga* species essentially have the same effects as the whole extract.

Ingredients or groups of ingredients to be particularly taken into consideration are the following: triterpenes, e.g., acteol and cimicigenol derivatives; polyphenols, such as caffeic acid and its derivatives, chlorogenic acid, piscidic acid, fucinolic acid, ferulic and isoferulic acid, cimicifugic acids; formononetine; alkaloids, e.g. cytisine and methylcytisine.

These ingredients are, besides in *Cimicifuga racemosa*, also found in additional *Cimicifuga* species such as, e.g., *C. foetida, C. dahurica, C. heracleifolia, C. simplex, C. japonica, C. europaea, C. acerina, C. elata, C. rubifolia*.

These further *Cimicifuga* species may thus also be used for producing extracts, and thus medicaments against the sexual hormone-related disorders of the uro-genital tract that are being mentioned in the context of the present invention.

Preferably rhizoma, roots, stalks, leaves and/or petals of the plants are used for producing the extracts.

The invention claimed is:

1. A method for alleviating a prostatic disorder selected from the group consisting of benign and malignant prostate hyperplasy comprising the step of administering an estrogen-type organoselective medicament to alleviate the prostatic disorder, the medicament comprising an extract from a *Cimicifuga* species.

2. The method of claim 1 wherein the *Cimicifuga* species is selected from the group consisting of: *C. racemosa, C. foetida, C. dahurica, C. heracleifolia, C. simplex, C. japonica, C. europaea, C. acerina, C. elata, C. rubifolia*.

3. The method of claim 2 wherein the *Cimicifuga* species is *C. racemosa*.

4. The method of claim 1 wherein the extract is produced from a *Cimicifuga* species by extraction with an organic solvent, such that the method alleviates the prostatic disorder.

5. The method of claim 1 wherein the extract is produced from a *Cimicifuga* species by extraction with a mixture of an organic solvent and water, such that the method alleviates the prostatic disorder.

6. The method of claim 1 wherein the extract is produced from a *Cimicifuga* species by extraction with supercritical $CO_2$, such that the method alleviates the prostatic disorder.

* * * * *

UNITED STATES PATENT AND TRADEMARK OFFICE
CERTIFICATE OF CORRECTION

PATENT NO. : 7,413,754 B2  Page 1 of 1
APPLICATION NO. : 10/490190
DATED : August 19, 2008
INVENTOR(S) : Wolfgang Wuttke et al.

It is certified that error appears in the above-identified patent and that said Letters Patent is hereby corrected as shown below:

Column 1, line 21 - after the word "it," the letters "i. a." should be deleted;
Column 1, line 22 - before the word "urethra" the word --the-- should be inserted;
Column 1, line 24 - the word "have" should be changed to "has;"
Column 1, line 33 - the word "facilitated" should be changed to "facilitates;"
Column 2, line 12 - the phrase "regulate down" should be changed to "down regulate;"
Column 2, line 16 - the phrase "regulate up" should be changed to "up regulate" and the phrase "regulated down" should be changed to "down regulated;"
Column 3, line 14 - the phase "As regards" should be changed to "Regarding."

Signed and Sealed this

Sixteenth Day of December, 2008

JON W. DUDAS
*Director of the United States Patent and Trademark Office*